United States Patent [19]

Collins et al.

[11] 4,004,029
[45] Jan. 18, 1977

[54] COMPOSITIONS AND METHOD FOR TREATING EPILEPSY AND CONVULSIONS

[75] Inventors: Robert James Collins; Charles E. Coverdale, both of Portage, Mich.

[73] Assignee: The Upjohn Company, Kalamazoo, Mich.

[22] Filed: Sept. 8, 1975

[21] Appl. No.: 610,939

Related U.S. Application Data

[60] Division of Ser. No. 469,485, May 13, 1974, abandoned, which is a continuation of Ser. No. 347,794, April 4, 1973, abandoned.

[52] U.S. Cl. .............................................. 424/325
[51] Int. Cl.² ...................................... A61K 31/13
[58] Field of Search ................ 424/325; 260/558 P

[56] References Cited

UNITED STATES PATENTS 3,293,252  12/1966  Fried et al. ...................... 260/558 P

FOREIGN PATENTS OR APPLICATIONS 1,215,839  5/1966  Germany ............................ 260/558
1,198,019  7/1970  United Kingdom ................. 260/558

OTHER PUBLICATIONS

"Anti-Ulcer Agents," Moffett et al., J. Med. Chem., vol. 14, pp. 963-968 (1971).

*Primary Examiner*—Stanley J. Friedman
*Attorney, Agent, or Firm*—John J. Killinger; Roman Saliwanchik

[57] ABSTRACT

Compounds of the formula

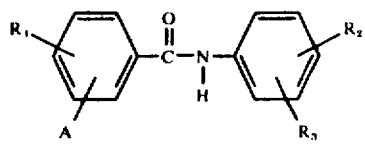

wherein $R_1$ and $R_2$ are each hydrogen or lower alkyl, $R_3$ represents lower alkyl and A is a monovalent group of formula:

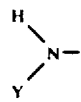

wherein Y is hydrogen or the acyl radical of a hydrocarbon carboxylic acid having from 2 to 18 carbon atoms, inclusive, are employed as anticonvulsants in treating mammals, including humans.

Novel compounds within the scope of the above formula are also disclosed, wherein $R_1$ is specifically lower alkyl and provided that $R_1$ is located in a position ortho or meta to the substituent group A when $R_2$ is hydrogen. Disclosed also are novel intermediate compounds for preparing the above-described novel compounds of the invention, which correspond thereto but wherein the group A is replaced by a nitro-group.

19 Claims, No Drawings

COMPOSITIONS AND METHOD FOR TREATING EPILEPSY AND CONVULSIONS

This is a division of application Ser. No. 469,485, filed May 13, 1974, now abandoned, a continuation of Ser. No. 347,794 filed 4/4/73, now abandoned.

BACKGROUND OF THE INVENTION

1. Field of the Invention

The invention concerns a method of using aminobenz amides as anticonvulsants, novel nitrobenzamides and amino benzamides prepared therefrom and compositions thereof which are useful anticonvulsants. More particularly, the invention concerns novel N'-alkyl-substituted nitrobenzamides, novel and known N'-alkyl-substituted aminobenzamides and methods of using the latter compounds.

2. Description of the Prior Art

The following 2-aminobenzanilides have been described previously; 2-aminobenzanilide (Beilstein 14, 320; 14–11, 210); N'-(2-methylphenyl)-2-aminobenzamide (Beilstein 14, 321); N'-methyl-N'-phenyl-2-amino-3-methylbenzamide [J Chem. Soc., 4110, (1959)]; N'-(methylphenyl)-2-amino-5-methylbenzamides [J. Ind. Chem. Soc., 33, 365, (1956)]; and N'-(2,6-dimethylphenyl)-2-aminobenzamide (Bull. Soc. Chim. France, 1962, 487). None of the above described compounds have been described as possessing anticonvulsant, sedative or muscle relaxant properties.

U. S. Pat. No. 3,443,833 described the use of 2-amino-4'-(diethylamino)-2'-methylbenzanilide as an anticonvulsant.

We have found a particular group of N,-alkyl-substituted aminobenzamides to be particularly useful anticonvulsants in that they show a high order of anticonvulsive activity coupled with a relatively low order of toxicity and only mild sedative properties. This makes the method of our invention particularly advantageous for the long term treatment, for example, of epilepsy in humans since many of the prior art medicaments for treating epilepsy sedate the patient to an undesirable degree, or possess other unwanted side effects at effective anticonvulsant dosage levels.

The compounds of our invention herein disclosed are particularly advantageous anticonvulsants in that they show anticonvulsant activity on the order of at least 2 to 3 times that of diphenylhydantoin or 2-amino 4'-(diethylamino)-2'-methylbenzanilide, both of which are widely known anticonvulsants. At the effective dosage levels of the compounds of the invention, fewer undesirable side effects are found.

SUMMARY OF THE INVENTION

The invention comprises a method of controlling convulsions and seizures in mammals in need of such therapy which comprises administering an effective amount of a compound of formula:

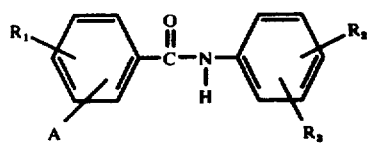

wherein $R_1$ and $R_2$ are each selected from hydrogen and lower alkyl; $R_3$ is lower alkyl and A is a monovalent group of formula:

wherein Y is selected from hydrogen and the acyl radical of a hydrocarbon carboxylic acid having from 2 to 18 carbon atoms, inclusive; to said mammals.

The invention also comprises novel compounds within the scope of formula (I) having the specific formula:

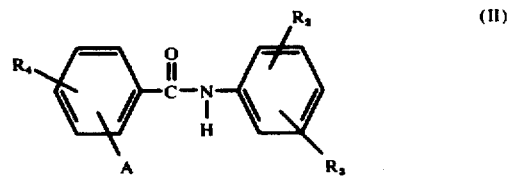

wherein A, $R_2$ and $R_3$ are as previously defined, $R_4$ is lower alkyl and provided that when $R_2$ is hydrogen, $R_4$ is located in one of the positions ortho and meta to group A. The invention also comprises novel intermediate compounds for preparing the compounds (II) of the invention, which are the corresponding nitrobenzamides of formula (II) wherein the group A has been replaced by a nitro group.

The novel compounds (II) of the invention are useful as mild sedatives and muscle relaxants in treating mammals, including humans. The compounds (II) are particularly useful anticonvulsants in treating animals, including humans, requiring such therapy.

The nitrobenzaminides having a formula corresponding to the formula (II) but wherein A is replaced with a nitro group are useful intermediate compounds for preparing the compounds of formula (II).

The invention also comprises compositions useful for and methods of controlling convulsions and seizures in mammals in need of such therapy, which comprises administering an effective amount of a compound of the formula (I) above to said mammals. A particularly preferred embodiment of the method of the invention is the process for the treatment of epilepsy in humans which comprises administering an effective amount of compounds (I) and most preferably N'-(2,6-dimethylphenyl)-2-amino-3-methylbenzamide to humans afflicted with epilepsy.

The term "lower alkyl" is used herein in its conventional sense as meaning the monovalent moiety obtained upon removal of a hydrogen atom from a saturated hydrocarbon, said hydrocarbon having from 1 to about 6 carbon atoms, inclusive. Illustrative of lower alkyl are groups such as methyl, ethyl, propyl, butyl, pentyl, hexyl and isomeric forms, thereof.

The term "acyl radical of a hydrocarbon carboxylic acid having from 2 to 18 carbon atoms, inclusive" means the monovalent moiety of formula:

wherein E is hydrocarbyl of from 1 to about 7 carbon atoms, inclusive, and which is obtained upon removal of the hydroxyl group from a hydrocarbon carboxylic acid. Illustrative of acyl radicals of a hydrocarbon carboxylic acid are the acyl radicals of (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids and the like; (b) saturated or unsaturated alicyclic carboxylic acids, for example, cyclobutane carboxylic acid, cyclopentanecarboxylic acid, cyclopentenecarboxylic acid, methylcyclopentenecarboxylic acid, cyclohexanecarboxylic acid, dimethylcyclohexenecarboxylic acid, dipropylcyclohexanecarboxylic acid, and the like; (c) saturated or unsaturated alicyclic aliphatic carboxylic acids, for example, cyclopentaneacetic acid, cyclopentanepropionic acid, cyclohexanebutyric acid, methylcyclohexaneacetic acid, and the like; (d) aromatic carboxylic acids, for example benzoic acid, toluic acid, naphthoic acid, ethylbenzoic acid, isobutylbenzoic acid, methylbutylbenzoic acid, and the like; and (e) aromatic-aliphatic carboxylic acids, for example phenylacetic acid, phenylpropionic acid, phenylvaleric acid, cinnamic acid, phenylpropionic acid, and naphthylacetic acid, and the like.

The term "convulsion" is used herein as meaning the violent involuntary contraction or repeated contractions of the voluntary muscles.

The term "seizure" is used herein as meaning the physical affliction characterized by transient clouding of consciousness, generally associated with a disturbance in the electrical activity of the cortex of the brain. Illustrative of such seizures are those associated with petit mal epilepsy.

The term "epilepsy" is used herein in its broadest sense, for example, as inclusive of grand mal, petit mal, and psychic equivalent or psychomotor attacks.

The term "effective amount" as used throughout the specification and claims means that minimum quantity which prevents or blocks a convulsion or seizure as previously defined. In general, an effective amount is within the range of from about 0.5 mg. to about 5.0 mg. for each kilogram of body weight of the mammal to be treated according to the method of the invention.

DETAILED DESCRIPTION OF THE INVENTION

Compounds of the formula (I) above wherein Y is specifically hydrogen are prepared by reduction of the correponding nitrobenzanilide of formula:

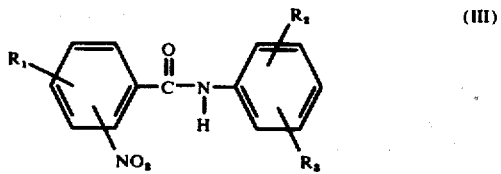

(III)

wherein $R_1$, $R_2$ and $R_3$ are as defined above.

The reduction of compounds (III) may be carried out by any of the well known methods for reducing a nitrobenzamide to the corresponding aminobenzamide. A convenient method is by catalytic hydrogenation.

The catalytic hydrogenation of compounds of formula (III) is readily carried out by reacting the nitrobenzamide (III) with hydrogen in the presence of an inert organic solvent and a hydrogenation catalyst.

The term "inert organic solvent" as used herein means an organic solvent for the reactants which does not react with the reactants or interfere in any way with the desired course of the reaction. Illustrative of inert organic solvents are aliphatic organic solvents such as n-hexane, cyclohexane and the like; aromatic organic solvents such as benzene, toluene, xylene and the like chlorinated aliphatic and aromatic organic solvents such as methylene chloride, chloroform, carbon tetrachloride, chlorobenzene and the like. Preferred organic solvents for carrying out the catalytic hydrogenation of nitrobenzamide (III) are the lower alkanols such as methanol, ethanol, propanol, butanol, pentanol, and hexanol, including the isomeric forms thereof. Sufficient solvent is employed to provide a concentration of the starting nitrobenzamide (III) of from about 5 percent to about 25 percent by weight.

Hydrogenation catalysts are illustrated by the noble metals, such as platinum, palladium, rhodium and the like, and by Raney Nickel. Preferred as hydrogenation catalysts herein are the supported catalysts such as, for example, platinum on carbon and palladium on carbon. The proportion of catalyst employed is from about 1 to about 25 parts by weight of reaction mixture.

Although any conventional hydrogenation apparatus may be employed, a convenient apparatus provides a low pressure hydrogenation; i.e., one providing for from 1 to 100 atmospheres of hydrogen gas pressure. The hydrogenation proceeds satisfactorily at ambient temperatures, i.e., circa 25° C. but the rate of reaction may be advantageously speeded by heating the reaction mixture up to about 50° C.

The hydrogen gas pressure employed during hydrogenation is within the range of from 1 atmosphere to about 100 atmospheres, and preferably is within the range of from about 2 to about 50 atmospheres of pressure.

An indication that hydrogenation is complete is the cessation of hydrogen gas consumption. Upon completion of hydrogenation the desired compounds of formula (I) wherein Y is specifically hydrogen are separated from the reaction mixture by conventional methods such as by filtration to remove catalyst residue, evaporation of solvent and crystallization from solvent extracts.

Nitrobenzamides of formula (III) above are readily prepared by the N-acylation of the corresponding alkyl substituted aniline (IV) with an appropriate nitrobenzoyl halide (V). The reaction is conveniently illustrated by the schematic formula:

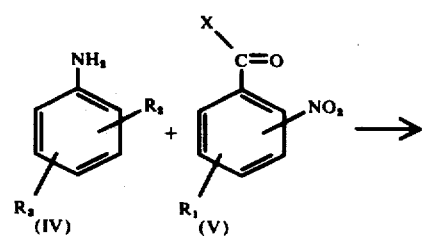

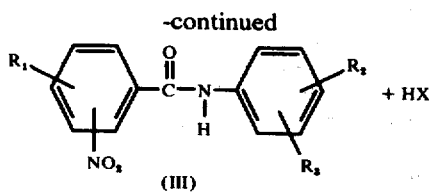

wherein $R_1$, $R_2$ and $R_3$ are as previously described and X is halogen. The term "halogen" as used herein is embracive of chlorine, bromine, iodine and fluorine.

The preparation of compounds (III) is carried out by admixture of the reactants (IV) and (V) in stoichiometric proportions, i.e., substantially equimolar proportions. Preferably the reactants (IV) and (V) are brought together in the presence of an inert organic solvent, as previously defined. The proportion of inert organic solvent employed is not critical, but preferably is such that the nitrobenzoyl halide (V) is placed in solution. Preferred inert organic solvents are the chlorinated aliphatic and aromatic solvents such as methylene chloride and the like.

The acylation described above proceeds satisfactorily over a broad range of temperature, i.e., from about −20° C. to reflux temperature of the particular reaction mixture. In general, the acylation is carried out satisfactorily at temperatures below about 150° C. and preferably within the range of from about 25° C. to about 50° C.

A by-product of the N-acylation reaction described above is the halogen acid corresponding to the particular halide acylating agent. In a preferred embodiment of the above described acylation, this halogen acid by-product is removed from the reaction mixture as it forms. The removal of halogen acid by-product may be accomplished by conventional methods, for example, by adding an acid acceptor compound such as a tertiary amine to the acylation reaction mixture. Illustrative of tertiary amines which may be employed are trimethylamine, triethylamine, tributylamine and the like. Preferred as an acid acceptor compound is pyridine.

The reaction which occurs during N-acylation is exothermic in nature. The exotherm may be controlled by conventional methods, such as by cooling the reaction mixture, or by the gradual addition of the aniline reactant (IV) to the halide acylating agent (V).

Cessation of continued exotherm is indicative of completion of the N-acylation. Upon completion of the N-acylation, the desired product compound of formula (III) wherein Y is specifically hydrogen may be separated from the reaction mixture by conventional methods, for example, by solvent extraction and crystallization techniques.

The alkyl-substituted aniline starting compounds of formual (IV) are well known compounds as is their preparation. Illustrative of the compounds (IV) are o-, m- and p- methylaniline; o-, m- and p- ethylaniline; o-, m- and p- isopropylaniline; o-, m- and p- tert-butulaniline; o-, m- and p-n-pentylaniline; o-, m- and p-n-hexylaniline; 2,6-dimethylaniline, 2,6-diethylaniline, 3,5-diethylaniline, 2,4-diisopropylaniline, 2,5-diisopropylaniline, 2-butyl-5-methylaniline and the like.

The nitrobenzoyl halides (V) are also well known as is their preparation; see for example the method set forth in Acta. Chem. Scand. 14, 2049, (1960). Illustrative of the reactants (V) are o-, m- and p- nitrobenzoyl chloride; o-, m- and p- nitrobenzoyl bromide; o-, m- and p- nitrobenzoyl iodide; 3-methyl-2-nitrobenzoyl chloride, 4-methyl-2-nitrobenzoyl chloride, 3-nitro-4-propylbenzoyl chloride, 3-nitro-4-pentylbenzoyl chloride, 3-nitro-5-methylbenzoyl chloride, 3-nitro-2-ethylbenzoyl chloride, 4-nitro-4-methylbenzoyl chloride, and 4-nitro-2-hexylbenzoyl chloride.

Compounds of formula (I) wherein Y is specifically an acyl radical of a hydrocarbon carboxylic acid having from 2 to 18 carbon atoms, inclusive, are prepared by acylating the nitrogen in the substituent group A of a corresponding compound (I) wherein Y is hydrogen. The acylation is readily carried out by conventional and well known methods, such as by reacting substantially equimolar proportions of the compounds (I) wherein Y is hydrogen and an appropriate hydrocarbon carboxylic acid halide of formula:

(VI)

wherein E and X are as defined previously. The acylation reaction is advantageously carried out by admixture of the reactants in the presence of an inert organic solvent as previously defined. Preferred solvents are benzene, ether, tetrahydrofuran, and toluene. The quantity of solvent employed is not critical, but preferably is sufficient to solubilize the reactants.

The acylation of the compounds (I) proceeds satisfactorily at ambient temperatures, but advantageously is carried out at a temperature within the range of from about 25° C. to about 100° C.

Completion of the acylation may be determined by conventional analytical methods. For example, infrared analysis will indicate the disappearance of starting materials and the presence of the desired products. Upon completion of the reaction, the desired product compounds (I) wherein Y is an acyl group are separated from the reaction mixture by conventional methods, for example, by filtration, solvent extraction and crystallization techniques.

The acid halide compounds (VI) are generally well known and are prepared by a wide variety of known methods; see for example, Rodd, Chemistry of Carbon Compounds, Elsevier Pub. Co., N. Y., Vol. Ia, pg. 588 and Vol. IIIa, pg. 5–7, (1951). One method is by reaction of an appropriate hydrocarbon carboxylic acid with a phosphorous halide such as phosphorus pentachloride or phosphorous tribromide. Examples of appropriate hydrocarbon carboxylic acids are those listed above.

Illustrative of the acid halides (VI) are acetonyl chloride, propionyl chloride, isobutyryl chloride, valeryl chloride, isovaleryl chloride, neopentylacetyl chloride, hexanoyl chloride, heptanoyl chloride, stearoyl chloride, palmitoyl chloride, phenylacetyl chloride, benzoyl chloride, tolyl chloride, cyclopentanepropionyl chloride, cyclohexaneacetyl chloride, acrylyl chloride, crotonyl chloride, 2-hexynoyl chloride, 2-octynoyl chloride and like acid halides.

An alternative method of preparing the acylates of Compound (I) is by the method of Chu, J.A.C.S., 67, 1862–3 which comprises employing the anhydride of the carboxylic acid as the acylating agent.

The following examples describe the manner and process of making and using the invention and set forth the best mode contemplated by the inventors of carrying out the invention, but are not to be constured as limiting.

EXAMPLE 1

N'-(2,6-dimethylphenyl)-3-methyl-2-nitrobenzamide

An appropriate reaction vessel is charged with 19.96 grams (0.1 mole) of 3-methyl-2-nitrobenzoyl chloride [prepared according to the method described in Acta Chem. Scand., 14, 2049 (1960)]and 55 ml. of methylene chloride. A solution of 8.69 grams (0.11 mole) of pyridine in 25 ml. of methylene chloride is added with mixing. To the resulting mixture there is adapted dropwise with stirring over a period of about four minutes, 12.12 grams (0.1 mole) of 2,6-dimethylaniline in 25 ml. of methylene chloride. During the addition, the reaction mixture warms to reflux temperture. Upon the completion of 2,6-dimethylaniline addition, th reaction mixture is allowed to cool while being stirred overnight at ambient temperatures. At the end of this period, 250 ml. of 6N hydrochloric acid is added and the resulting mixture extracted with a mixture of ether-chloroform. The extract is washed with brine, dried over anhydrous sodium sulfate and evaporated. The solid residue is recrystallized from methanol after decolorization with Darco G-60 to give 21.5 grams of N'-(2,6-dimethylphenyl)-3-methyl-2-nitrobenzamide in the form of yellow crystals, M.P. 180° C. to 181.5° C.. An additional 3.57 grams of product, M.P. 177° C. to 180° C. (total 24.72 grams; 87 percent of theory) is obtained by concentration of the mother liquors.

The identity of the product compound is confirmed by infra-red spectral analysis and elemental analysis.

Similarly, repeating the above procedure but replacing the 3-methyl-2-nitrobenzoyl chloride as used therein with an equal molar proportion of o-nitrobenzoyl chloride, there is obtained N'-(2,6-dimethylphenyl)-2-nitrobenzamide.

Similarly, repeating the above procedure but replacing the 2,6-dimethylaniline as used therein with an equal molar proportion of 4-propylaniline and 3-hexylaniline, respectively, there is obtained N'-(4-propylphenyl)3-methyl-2-nitrobenzamide and N'-(3-hexylphenyl)-3-methyl-2-nitrobenzamide, respectively.

EXAMPLE 2

N'-(2,6-dimethylphenyl)-2-amino-3-methylbenzamide

An appropriate Parr low pressure apparatus (Parr Instrument Co., Moline, Illinois) is charged with 19.0 grams (0.067 mole) of N'-(2,6-dimethylphenyl)-3-methyl-2-nitrobenzamide (Example 1., supra), 0.5 grams of 10 percent palladium on charcoal and 150 ml. of methanol. The reaction vessel is purged with hydrogen gas and then charged with 50 psi (gauge) hydrogen gas. The reaction mixture is then continuously agitated. After 2.5 hours, the remaining hydrogen is evacuated from the reaction vessel, and the reaction mixture is filtered to remove catalyst residues. The filtrate is evaporated and the residue dissolved in a mixture of benzene-cyclohexane (1:1, v/v). Upon concentration of the solution, a precipitate is obtained. Upon separating and drying the precipitate, there is obtained 16.89 gm. (99.5% of theory) of N'-(2,6-dimethylphenyl)-2-amino-3-methylbenzamide in the form of colorless crystals, M.P. 133.5° C. to 136° C. Repeated recrystallizations provide analytical samples having a M.P. of 146° C. to 147° C.

Identity of the product structure is confirmed by infrared spectral analysis and elemental analysis.

Similarly, repeating the above procedure but replacing the N'-(2,6-dimethylphenyl)-3-methyl-2-nitrobenzamide as used therein with an equal molar proportion of N'-(2,6-dimethylphenyl)-2-nitrobenzamide; N'-(4-propylphenyl)-3-methyl-2-nitrobenzamide and N'-(3-hexylphenyl)-3-methyl-2-nitrobenzamide, respectively, (all of which are prepared according to the method of Example 1, supra.) there is obtained N'-(2,6-dimethylphenyl)-2-aminobenzamide; N'-(4-propylphenyl)-2-amino-3-methylbenzamide and N'-(3-hexylphenyl)-2-amino-3-methylbenzamide, respectively.

When injected intraperitoneally into mice, the $LD_{50}$ of the N'-(2,6-dimethylphenyl)-2-amino-3-methylbenzamide prepared in Example 2., supra., is shown to be 297 mg./kg. This compared favorably to diphenylhydantoin ($LD_{50}$ 200 mg./kg.).

EXAMPLE 3

N'-(2,6-dimethylphenyl)-2-acetylamine-3-methylbenzamide

An appropriate reaction vessel is charged with 16.8 gms. (0.06 moles) of N'-(2,6-dimethylphenyl)-2-amino-3-methylbenzamide (prepared according to the method of Example 2., supra.), 6.10 gms. (0.06 moles) of acetic anhydride and 100 ml. of dry benzene. The mixture is refluxed on a steam bath for about 1 hour. At the end of this period, solvent is removed by distillation under reduced pressure and the residue is washed with cold water and filtered. The residue is recrystallized from a mixture of acetone-methanol (1:1, v/v to give N'-(2,6-dimethylphenyl)-2-acetylamine-3-methylbenzamide in the form of crystals.

The compounds of Formula (I) may be suitably formulated as the essential active ingredient in pharmaceutically acceptable carriers, offering an effective amount of the compounds of Formula (I) in liquid and solid forms for oral, rectal and parenteral administration to control convulsions and seizures in mammals.

Compositions intended for oral use as tablets, aqueous or oily suspensions, powders, granules, emulsions, syrups, elixirs, capsules and like forms, the preparation of which are well known in the art. Such compositions may contain one or more sweetening, flavoring, coloring or preserving agents to provide an elegant and palatable pharmaceutical preparation.

The solid oral forms, in addition to containing the essential active ingredient may contain, additionally, suitable pharmaceuitcal carriers, i.e., excipients, such as inert diluents, for example, calcium carbonate, sodium carbonate, lactose, calcium phosphate, sodium phosphate and the like; granulating and disintegrating agents, for example, maize starch or alginic acid; binding agents such as starch, gelatine or acacia, lubricants such as magnesium stearate, stearic acid, talc and the like.

Tablet forms may be uncoated or coated, by known methods, to provide sustained release of essential active ingredient over a prolonged period of time, i.e., enteric coated.

Dispersible powder and granule forms, such as freeze dried forms suitable for extemporaneous preparation of an aqueous suspension, by the addition of a fluid carrier containing active ingredient, may be compounded with dispersing, wetting, suspending and preserving agents.

Properly formulated by methods known in the art, many of the oral solid forms may be administered rectally. Preferably, however, the compositions of the invention for rectal use are prepared by mixing the essential active ingredient with a pharmaceuitcally acceptable non-irritating excipient which is solid at ordinary room temperatures but liquid at rectal temperature. Illustrative of such excipients are cocoa butter and polyethylene glycols. The mixed composition is then cast in the form of a rectal suppository.

Aqueous suspensions of the essential active ingredient for oral administration are prepared, for example, by admixture with pharmaceutically acceptable carriers, i.e., excipients such as suspending agents like methylcellulose, gum acacia, gum tragacanth, sodium carboxymethylcellulose and the like; preservatives, flavoring and sweetening agents.

Parenteral compositions of the invention are prepared by conventional methods, i.e., as sterile injectable aqueous suspensions which may contain in addition to active essential ingredient, pharmaceutically acceptable wetting, buffering, pH adjusting, dispersing, suspending and preserving agents. The parenteral compositions of the invention may be administered intramuscularly, subcutaneously or intraperitoneally.

Each of the pharmaceutical forms which comprises the compositions of the invention are preferably formulated so as to provide from about 25 mg. to about 250 mg. of compounds of the formula (I) as the essential active ingredient per unit dose. Each dose is administered, generally, from 1 to 4 times a day so as to provide a total daily dose of from about 25 mg. to about 1000 mg. with single dosages ranging from about 25 mg. to about 250 mg. The dosage can, of course, be adjusted by the attending physician with respect to age, weight, and affliction of the recipient being treated.

EXAMPLE 4

Aqueous Oral Suspension

An aqueous oral suspension is prepared from the following amounts and types of ingredients:

| | |
|---|---|
| N'-(2,6-dimethylphenyl)-2-amino-3-methylbenzamide (Example 2., supra.) | 2.5 gm. |
| microcrystalline cellulose | 1.1 gm. |
| sodium carboxymethylcellulose | 0.9 gm. |
| orange flavor | 0.45 gm. |
| purified water q.s. | 100 ml. |

The microcrystalline cellulose is dispersed in the water, the sodium carboxymethylcellulose and orange flavor are added and dissolved by means of a high shear mixer. The N'-(2,6-dimethylphenyl)-2-amino-3-methylbenzamide is added and the suspension homogenized.

One to two teaspoons (5 ml.) daily is useful in controlling convulsions.

EXAMPLE 5

Tablets

A lot of 10,000 tablets, each containing 100 mg. of N'-(2,6-dimethylphenyl)-2-amino-3-ethyl benzamide is prepared from the following types and amounts of ingredients:

| | |
|---|---|
| N'-(2,6-dimethylphenyl)-2-amino-3-methylbenzamide | 1,000 gm. |
| dicalcium phosphate | 1,500 gm. |
| methylcellulose, U.S.P. (15 cps) | 60 gm. |
| talc | 150 gm. |
| corn starch | 200 gm. |
| calcium stearate | 12 gm. |

The N'-(2,6-dimethylphenyl)-2-amino-3-methylbenzamice and dicalcium phosphate are mixed well, granulated with a 7.5 percent solution of methylcellulose in water, passed through a No. 8 screen and dried carefully. The dried granules are passed through a No. 12 screen, mixed thoroughly with the talc, starch and calcium stearate and compressed into tablets.

These tablets are useful for treatment of convulsions and seizures at a dose of 1-2 tablets a day.

EXAMPLE 6

Suppository

One thousand suppositories, each containing 100 mg. of active ingredient and weighing 2.5 gm., for rectal administration, are prepared from the following types and amounts of ingredients:

| | |
|---|---|
| N'-(2,6-dimethylphenyl)-2-amino-2-methylbenzamide | 100 gm. |
| propylene glycol | 165 gm. |
| polyethylene glycol 4000 q.s. | 2,500 ml. |

The N'-(2,6-dimethylphenyl)-2-amino-3-methylbenzamide is added to the propylene glycol and dispersed. The polyethylene glycol 4000 is melted and added to the dispersion. The suspension is poured into molds and cooled to allow solidifications. These suppositories are useful for controlling convulsions at a dose of 1 suppository 1-3 times a day.

EXAMPLE 7

Parenteral Aqueous Suspension

A sterile aqueous suspension for parenteral administration containing 50 mg. of N'-(2,6-dimethylphenyl)-2-amino-3-methylbenzamide in each 1 ml. is prepared from the following types and amounts of ingredients:

| | |
|---|---|
| N'-(2,6-dimethylphenyl)-2-amino-3-methylbenzamide | 50 gm. |
| polysorbate 80 | 8 gm. |
| sodium chloride | 18 gm. |
| benzyl alcohol | 18 gm. |
| water for injection q.s. | 1,000 ml. |

A dose of 1-2 ml. daily is useful in controlling convulsions.

EXAMPLE 8

Repeating the procedure of each of Examples 4-7, inclusive, but replacing the N'-(2,6-dimethylphenyl)-2-amino-3-methylbenzamide active ingredient as used therein with each of the other aminobenzamide products of formula (I) prepared in Examples 2 and 3 supra., there is obtained a pharmaceutical composition useful in controlling convulsions.

The following examples illustrate the use of compounds of formula (I) in treating mammals.

EXAMPLE 9

Comparative Anti-Convulsant Activity

The protection against electroshock-induced seizures afforded by N'-(2,6-dimethylphenyl)-2-amino-3-methylbenzamide is determined according to the method of H. H. Keasling et al., J. Med. Chem. 8, 5–8, (1965).

Groups of six mice (Cartworth farms, male albino mice, weighing 18 to 22 gms. each) are each administered orally, (PO) or by intraperitoneal injection (IP) varying doses of N'-(2,6-dimethylphenyl)-2-amino-3-methylbenzamide Example 2, supra. suspended in 0.25 percent aqueous methylcellulose. After about thirty minutes, the mice are shocked via ear clip electrodes, with a 60-cycle electrical current for 0.2 second, using a current intensity of 25 milliamps. The number of mice protected against tonic extensor seizures is used as a quantal response to calculate the $Ed_{50}$, by the method of Spearman and Karper (see D. J. Finney, "Statistical Methodology in Biological Assay", Hofner Publishing Co., New York, N.Y. 1952, page 524). For control purposes, a group of six mice is similarly treated with diphenylhydantoin and shocked. Groups A-I, inclusive, are the groups treated with N'-(2,6-dimethylphenyl)-2-amino-3-methylbenzamide. The routes of administration, absorption times and the $ED_{50}$ calculations are reported in Table I below.

TABLE I

| Group | Administrative Route | Absorption Time (Minutes) | $ED_{50}$ |
|---|---|---|---|
| Diphenyl-hydantoin Treated Group (Control) | IP | 0.5 | 14 |
| A | IP | 0.5 | 7 |
| B | IP | 0.5 | 5.6 |
| C | PO | 0.5 | 10 |
| D | PO | 1 | 10 |
| E | PO | 2 | 10 |
| F | PO | 4 | 11 |
| G | PO | 8 | 32 |
| H | PO | 16 | 112 |
| I | PO | 24 | 178 |

The above TABLE I shows the effectiveness of a compound (I) in protecting the test animals against electroshock-induced seizures. This is generally accepted as indicative of useful anticonvulsant activity, i.e., in the clinical treatment of humans for grand mal epilesy. The table also shows N'(2,6-dimethylphenyl)-2-amino-3-methylbenzamide to be long acting.

Protection against seizures induced by electroshock is also shown in rats (Sprague Dawley male albino rats weighting 150 to 300 grams each). The testing procedure is identical to that used in Example 9 supra. except that the electroshock current intensity is increased from 25 to 150 milliamps to accommodate this larger species. Groups A–F, inclusive, received N'-(2,6-dimethylphenyl)-2-amino-3-methylbenzamide. The results are shown in Table II below.

TABLE II

| Group | Diphenylhydantoin (Control) | A | B | C | D | E | F |
|---|---|---|---|---|---|---|---|
| Administrative Route | IP | PO | PO | IP | IP | IP | IP |
| Absorption Time (Min.) | 30 | 30 | 30 | 30 | 60 | 240 | 480 |
| $ED_{50}$ (mg./kg.) | 8.0 | 2.5 | 7.0 | 4.5 | 2.5 | 4.5 | 7.1 |
| (95% confidence interval) | (5.4–12) | (16–10) | (43–11) | (3.0–6.8) | (1.5–4.2) | (3.1–6.6) | (4.6–11.8) |

The above table shows N'-(2,6-dimethylphenyl)-2-amino-3-methylbenzamide to be more potent on a milligram basis than diphenylhydantoin in anticonvulsive activity.

EXAMPLE 11

Effect on afterdischarge in the cat

Depression of electrically induced afterdischarges afforded by N'-(2,6-dimethylphenyl)-2-amino-3-methylbenzamide is determined according to the method of R. N. Strow and C. L. Mitchell, Electroenceph. Clin. Neurophysiol., 21:54 (1966).

Mongrel cats of either sex weighing 1.5–3.0 kg. are anesthetized with halothane. Two pair of stainless steel screw electrodes are placed bilaterally in the skull for stimulation and recording. The cats are paralyzed with decamethonium, artifically respired and after ninety minutes allowed to blow off the halothane. Afterdischarge is elicited by electrical stimulation across one pair of electrodes (5 second train of 1 millisecond pulses at 50 pulses per second at 5.0–10 milliamps). Duration of discharge is recorded from the second electrode pair. Two groups of controls are taken before test drug administration and duration of aferdischarge is measured after each dose of test drug. Each of 4 cats receives N'-(2,6-dimethylphenyl)-2-amino-3-methylbenzamide or diphenylhydantoin in increasing (total) doses of 2.5, 5.0, 10 and 20 mg./kg. intravenously.

TABLE III

| Dose (mg./kg.) | 0(Control I) | 0(Control II) | 2.5 | 5.0 | 10.0 | 20.0 | Relative Potency | 95% Confidence Limits |
|---|---|---|---|---|---|---|---|---|
| Diphenylhydantoin | 71 | 77 | 30 | 32 | 9 | 4 | 1 | — |
| N'-(2,6-dimethylphenyl)-2-amino-3-methylbenzamide | 69 | 84 | 31 | 27 | 4 | 2 | 1.42 | (0.35–3.64) |

The above Table III shows the effectiveness of N'-(2,6-dimethylphenyl)-2-amino-3-methylbenzamide in suppressing electrically-induced afterdischarge. It shows N'-(2,6-dimethylphenyl)2-amino-3-methylbenzamide to be 1.42 times more potent than diphenylhydantoin on a milligram basis in shortening the duration of the response.

EXAMPLE 12

Repeating the procedures of each of Examples 9–11, supra., but replacing the N'-(2,6-dimethylphenyl)-2-amino-3-methylbenzamide as used therein, in each case, with each of the other compounds of formula (I) prepared in Examples 2 and 3, supra., anticonvulsant activity is observed.

We claim:

1. A method of controlling convulsions and seizures in mammals in need of such therapy which comprises administering an effective amount of a compound of formula:

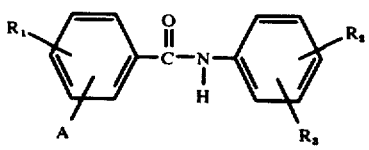

wherein $R_1$ and $R_2$ are each selected from hydrogen and lower alkyl; $R_3$ is lower alkyl and A is a monovalent group of formula:

wherein Y is selected from hydrogen and the acyl radical of a hydrocarbon carboxylic acid having from 2 to 18 carbon atoms, inclusive; to said mammals.

2. A method according to claim 1 wherein said mammal is human.

3. A method according to claim 1 wherein said compound is N'-(2,6-dimethylphenyl)-2-amino-3-methylbenzamide.

4. A method according to claim 1 wherein said effective amount is within the range of from about 0.5 mg. to about 5.0 mg. for each kilogram of body weight of said mammal.

5. A method according to claim 1 wherein N'-(2,6-dimethylphenyl)-2-amino-3-methylbenzamide is administered orally.

6. A method according to claim 1 wherein N'-(2,6-dimethylphenyl)-2-amino-3-methylbenzamide is administered parenterally.

7. A process for the treatment of epilepsy in humans which comprises administering an effective amount of a compound of formula:

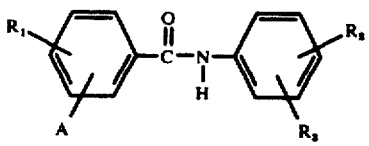

wherein $R_1$ and $R_2$ are each selected from hydrogen and lower alkyl; $R_3$ is lower alkyl and A is a monovalent group of formula:

wherein Y is selected from hydrogen and the acyl radical of a hydrocarbon carboxylic acid having from 2 to 18 carbon atoms, inclusive; to a human afflicted with epilepsy.

8. A process according to claim 7 wherein $R_1$ is alkyl, provided that $R_1$ is located in one of the positions ortho and meta to the substituent group A when $R_2$ is hydrogen.

9. A process for the treatment of epilepsy in humans which comprises administering an effective amount of N'-(2,6-dimethylphenyl)-2-amino-3-methylbenzamide to a human afflicted with epilepsy.

10. A process according to claim 9 wherein said effective amount is within the range of from about 0.5 gm. to about 5.0 mg. for each kilogram of body weight of said human.

11. A process according to claim 9 wherein said effective amount is an amount sufficient to provide a daily dose of from about 25 mg. to about 1000 mg.

12. A process according to claim 9 wherein the N'-(2,6-dimethylphenyl)-2-amino-3-methylbenzamide is administered orally.

13. A process according to claim 9 wherein the N'-(2,6-dimethylphenyl)-2-amino-3-methylbenzamide is administered parenterally.

14. A pharmaceutical composition useful in the control of convulsions and seizures in mammals comprising an effective amount of a compound of the formula:

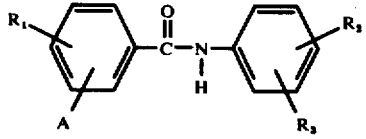

wherein $R_1$ and $R_2$ are each selected from hydrogen and lower alkyl; $R_3$ is lower alkyl and A is a monovalent group of formula:

wherein Y is selected from hydrogen and the acyl radical of a hydrocarbon carboxylic acid having from 2 to 13 carbon atoms, inclusive; and a pharmaecutically acceptable carrier.

15. A composition according to claim 14 wherein said carrier is a fluid, whereby said composition is suitable for oral administration.

16. A composition according to claim 14 wherein said carrier is a sterile fluid whereby said composition is suitable for parenteral administration.

17. A composition according to claim 14 wherein said carrier is a solid form, whereby said composition is suitable for oral and rectal administration.

18. A composition according to claim 14 wherein said carrier is in a unit dosage form, each unit containing from about 25 mg. to about 250 mg. of said compound.

19. A composition according to claim 14 wherein said compound is N'-(2,6-dimethylphenyl)-2-amino-3-ethylbenzamide.

* * * * *

UNITED STATES PATENT OFFICE
CERTIFICATE OF CORRECTION

Patent No. 4,004,029  Dated January 18, 1977

Inventor(s) Robert J. Collins; Charles E. Coverdale

It is certified that error appears in the above-identified patent and that said Letters Patent are hereby corrected as shown below:

Column 1, line 36, "aminoberzamides" should read --aminobenzamides--. Column 5, lines 59-60, "-butulaniline" should read -- -butylaniline --. Column 6, line 46, "5-7" should read --547--. Column 7, line 12, "adapted" should read --added--. Column 8, line 6, "nitroberzamide" should read --nitrobenzamide--; line 32, "v/v" should read --v/v)--. Column 9, line 66, "3-ethyl" should read --3-methyl--. Column 10, lines 10-11, "methylbenzamice" should read --methylbenzamide--. Column 11, line 7, "5-8" should read --548--; line 32, "Karper" should read --Karber--; line 45, "Diphenyl:" should read -- Diphenyl- --. Column 12, line 5, "above protecting" there should read --Example 10--. Table II, (95% confidence interval), under A, "(16-10)" should read --(16-40)--. Column 12, line 49, "aferdischarge" should read --afterdischarge--; line 54 should read --The duration of afterdischarge in seconds is depicted for each dose of the two drugs in the following Table III.--; line 64, "effictiveness" should read --effectiveness--. Column 14, line 52, "13" should read --18--; line 53, "pharmaecutically" should read --pharmaceutically--; line 68, "ethylbenzamide" should read --methylbenzamide--.

Signed and Sealed this

Third Day of May 1977

[SEAL]

Attest:

RUTH C. MASON
*Attesting Officer*

C. MARSHALL DANN
*Commissioner of Patents and Trademarks*